United States Patent [19]

Ingle, Jr.

[11] 4,236,109
[45] Nov. 25, 1980

[54] DIELECTRIC MONITORED COMPOSITE ASSEMBLY

[75] Inventor: Harold R. Ingle, Jr., Marietta, Ga.

[73] Assignee: Lockheed Corporation, Burbank, Calif.

[21] Appl. No.: 859,709

[22] Filed: Dec. 12, 1977

[51] Int. Cl.² ............... G01R 27/26; G01R 31/12; H01G 7/00

[52] U.S. Cl. .................. 324/61 P; 73/780; 324/54; 361/280

[58] Field of Search ............. 324/54, 61 R, 61 P, 324/52; 340/235; 73/88.5, 304 C, 336.5, 73, 768, 780; 361/280, 282, 283, 286, 301, 303, 313

[56] References Cited

U.S. PATENT DOCUMENTS

| | | | |
|---|---|---|---|
| 2,544,673 | 3/1951 | Haber | 324/61 P |
| 3,022,499 | 2/1962 | Ripepi | 324/61 R X |
| 3,037,165 | 5/1962 | Kerr | 324/61 P |
| 3,365,936 | 1/1968 | Hubin et al. | 324/61 P |
| 3,424,977 | 1/1969 | Krobath | 324/61 P |
| 3,588,689 | 6/1971 | Crawford | 324/52 |
| 3,678,378 | 7/1972 | Trott et al. | 324/61 R |
| 3,683,243 | 8/1972 | Rockliff | 361/286 |
| 3,779,071 | 12/1973 | Thomas et al. | 73/768 |
| 3,846,780 | 11/1974 | Gilcher | 361/280 X |
| 3,863,147 | 1/1975 | Erath | 324/61 R X |

FOREIGN PATENT DOCUMENTS

| | | | |
|---|---|---|---|
| 259300 | 6/1965 | Australia | 324/61 P |
| 1201308 | 8/1970 | United Kingdom | 324/61 R |

*Primary Examiner*—Gerard R. Strecker
*Attorney, Agent, or Firm*—A. L. Carter

[57] ABSTRACT

A dielectric probe comprising a pair of electrically conductive wires embeddable in or mountable on resin matrix composite materials for monitoring changes in the dielectric property of the composite structure due to moisture content therein, thermal spikes or fatigue degradations experienced thereby.

12 Claims, 5 Drawing Figures

DIELECTRIC MONITORED COMPOSITE ASSEMBLY

This invention relates to monitoring probes for resin matrix composite material, and more specifically to a pair of electrically conductive wires that can be embedded in or mounted on resin matrix composite material assemblies as capacitive plates for monitoring the dielectric properties thereof which in turn are indicative of mechanical property changes in the assembly due to moisture therein, subjection of the assembly to certain thermal environments or fatigue degradation.

It is known in the prior art that resin matrix composite materials are susceptible to degradation by significant changes in the mechanical properties and dimensional shapes of the materials due to moisture therein, thermal-spike excursions, and/or fatigue. The absorbed moisture in composites causes the resin to swell, inducing internal stresses. Moisture gradients and the resulting non-homogeneous swelling of the resin can lead to the formation of microcracks and delaminations. Additionally, water acts as a plasticizer in the polymer matrix, reducing the glass-transition temperature; that is, the temperature at which there is a dramatic loss of matrix modulus. At room temperature the difference between the matrix moduli for dry and wet laminates is not great. However, at elevated temperatures this difference becomes significant. Reduction in resin dominated static properties of as much as 50% have been observed at certain aircraft operating temperatures, and recent fatigue tests of bolted composite joints under reversed loading have revealed a reduction in life by a factor of 10 when the joints were subjected to moisture and tested at room temperature.

The result of all this is that moisture adversely affects resin matrix composite materials. It becomes necessary therefore to know how much moisture a given piece of composite structure has absorbed at a certain point in time, whether in the laboratory under controlled conditions, or in actual service under widely varying conditions. This becomes easy enough in the laboratory case (periodically weighing the specimens) if one accounts for such variables as moisture absorbing end tabs, bonding adhesive, sealant, paint, metal splice plates, fasteners, etc. However, the problem becomes more difficult if moisture distribution or gradients through the specimen thickness are required, since weighing establishes only the average moisture content in the specimen. Also, assemblies may be located in a field, away from equipment for weighing, and in the case of a larger fullscale aircraft structure, such as a flap, empennage, wing, etc., it must be removed from the aircraft for such weighing. Obviously, another method of moisture determination, that is accurate and convenient, is needed, since moisture content and distribution in composite materials in the field must be determined and monitored in order to extend the confidence level in current composite design methods to primary structural components.

During the curing of resins, dielectric measurement is a well established procedure in the prior art. The technique involves monitoring a resin undergoing curing for changes in the dielectric properties of the resin. These changes affect both the capacitance and the dissipation of the monitored material. There is presently known and available suitable instrumentation that can detect capacitance and dissipative changes and thus indirectly measure dielectric changes. Dielectric changes are directly related to the curing properties of the resin, therefore instant knowledge of such changes can be used to control the curing of a resin. Typically, the prior art probes comprise two small (0.5"×0.5") aluminum or copper foil "plates" separated, sandwich style, by the specimen being monitored. If a specimen is electrically conductive, as is the case of graphite composites, a thin polyimide sheet insulator is spaced between the probes and the specimen. Thus an average reading is taken throughout the thickness of the specimen. Use of the conventional prior art dielectric probes used in the curing of the resins are not suitable for the post manufacturing monitoring tasks as contemplated by this invention for the reasons that they would obstruct the flow of moisture into and out of the specimen or assemblies: they would present formidable problems in installation within the laminate for detection of moisture gradients throughout the laminate thickness; and it would be difficult to make them a permanent part of the structure without severely degrading the local mechanical properties of the laminate.

Attempts to find a post manufacturing monitoring probe showed that for various reasons, all conventional probe variants such as modification of the conventional cure-monitoring probes by perforation and dielectric coatings, as well as use of coated wire mesh, proved unsatisfactory. As a result of such unsatisfaction, and since capacitance is an inverse function of "plate" separation as well as of plate area, it has been found that use of small diameter coated wire probes of this invention as capacitive plates constitute a workable and viable probe design producing advantageous results.

Accordingly, it is an object of this invention to provide a dielectric probe for monitoring resin matrix composite material that is easy and inexpensive to fabricate and install.

A further object of this invention is to provide such a probe having an ability to read planar (single layer) conditions in a composite assembly.

Still another object of this invention is to provide such a probe that has relative immunity to capacitance changes with specimen temperature variations.

A further object of this invention is to provide such a dielectric probe having an ability to be buried in the composite laminate while maintaining integrity of insulation, does not impede resin flow while curing, does not impede moisture into or out of the cured composite, and does not require separately installed insulators when used in conductive composites.

Other objects and advantages will become apparent from the following description taken in connection with the accompanying drawings in which.

Generally stated, this invention comprises a pair of electrically conductive wires, each of which forms the plate of a capacitor, which when mounted on or embedded in a cured resin matrix composite material assembly and connected with appropriate circuitry constitutes a probe that results in dielectric property measurements of the composite that are indicative of the moisture content and structural integrity thereof.

Figure 1:
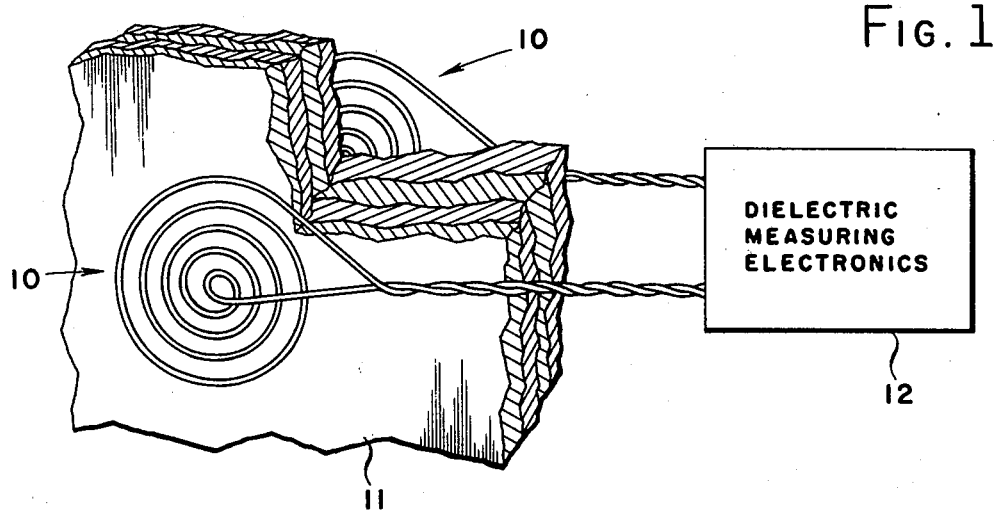
FIG. 1 shows one embodiment of this invention comprising a pair of spiral wound capacitor plates mounted on opposite sides of the composite specimen or workpiece.

More specifically, with reference to FIG. 1, there is shown a pair of electrically insulated coils of wire 10, each wound in such a manner as to produce a flat disc shape and mounted or adhered to each side of a resin matrix composite assembly 11. At least one end of the wire forming each coil or plate 10 extends outwardly to the end of composite 11 for connection to appropriate dielectric measuring equipment 12. The discs or coils 10 serve as capacitive plates, which when energized with alternating current function to measure the dielectric properties through the thickness of composite 11.

The plates 10 may be adhered or mounted on composite 11 after the lay-up and cure thereof by rubber cement or any other appropriate adherent, as well as the plates 10 may be mounted to the outer side walls of composite 11 during lay-up and prior to curing. In the latter case, the coil form of plates 10 is such that permit the resin of composite 11 to "bleed" in between or through the windings during curing. Likewise, whether the plates 10 are applied before or after curing of composite 11, moisture is allowed to be absorbed and desorbed uniformly in the area of the application of plates 10 so that the change in moisture content in composite 11 between plates 10, which changes the dielectric properties of composite 11, is indicative of the magnitude of moisture content that could be expected to be contained uniformly throughout composite 11. The approximate effective area of coil 10 as a capacitive plate is the product of the spiral length and the wire diameter.

It is also to be noted that should it be desired to obtain gradient measurements throughout the thickness of composite 11, the plates 10 can be placed in various locations between adjacent plies throughout the thickness of composite 11 during lay-up thereof. In this manner, dielectric values can be obtained between any pair of plates 10 throughout the thickness of composite 11.

Figure 2:
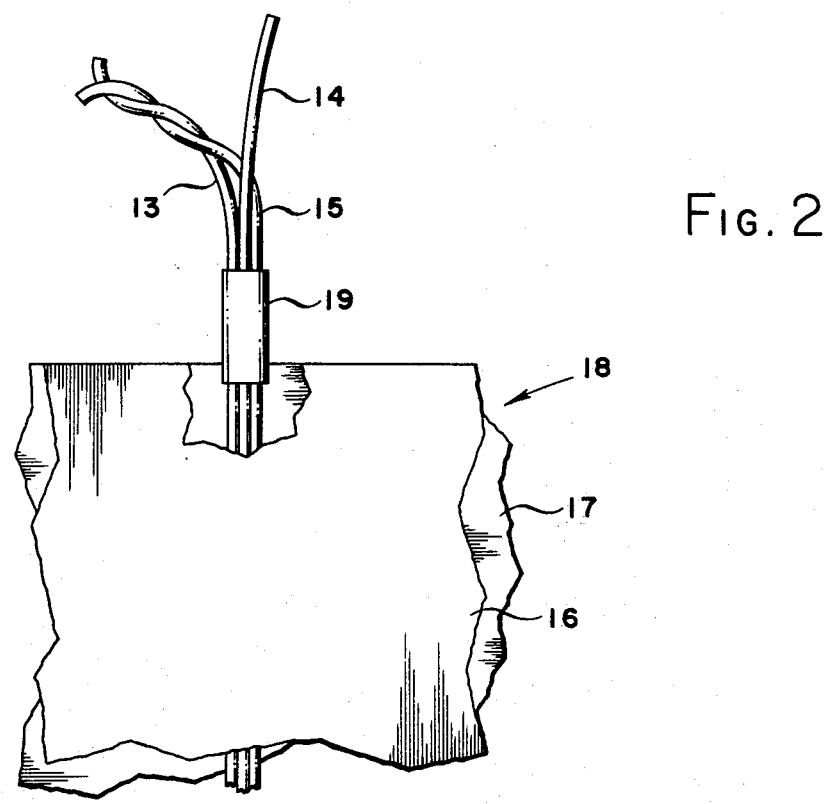
FIG. 2 shows another embodiment of this invention whereby the monitor probe wires are located in parallel fashion between two plies of the cured composite.

The embodiment shown in FIG. 2 comprises three parallel wires 13, 14 and 15 extending between adjacent plies 16 and 17 of a cured composite assembly 18. While preferable, but not mandatory, a shrink tubing member 19 or other appropriate type of protection can surround the wires and bridge the exit plane of the wires from the composite assembly 18 to assist in prevention of breakage of the wires at the exit plane due to bending.

In the case of three wire probes as shown in FIG. 2, the outer wires 13 and 15 are connected together at appropriate dielectric measuring instrumentation to form one capacitor plate while wire 14 serves as the other capacitor plate. Also, it is to be recognized that the use of a third wire as depicted is optional if increased capacitive levels are desired, or in other words, two wires can reflect dielectric property changes in the composite assembly 18 at the plane junction between plies 16 and 17 with two wires, but at lower capacitive levels.

While the arrangement depicted in FIG. 2 will be indicative of dielectric properties of the composite assembly 18 at the specific plane or level at the junction of adjacent plies 16 and 17, it is to be recognized that various dielectric gradients of composite assembly 18 can be obtained by location of additional probe assemblies at various locations between adjacent plies throughout the overall thickness; the probe wires being laid out in parallel fashion at the appropriate levels during lay-up of the composite prior to curing.

Figure 3:
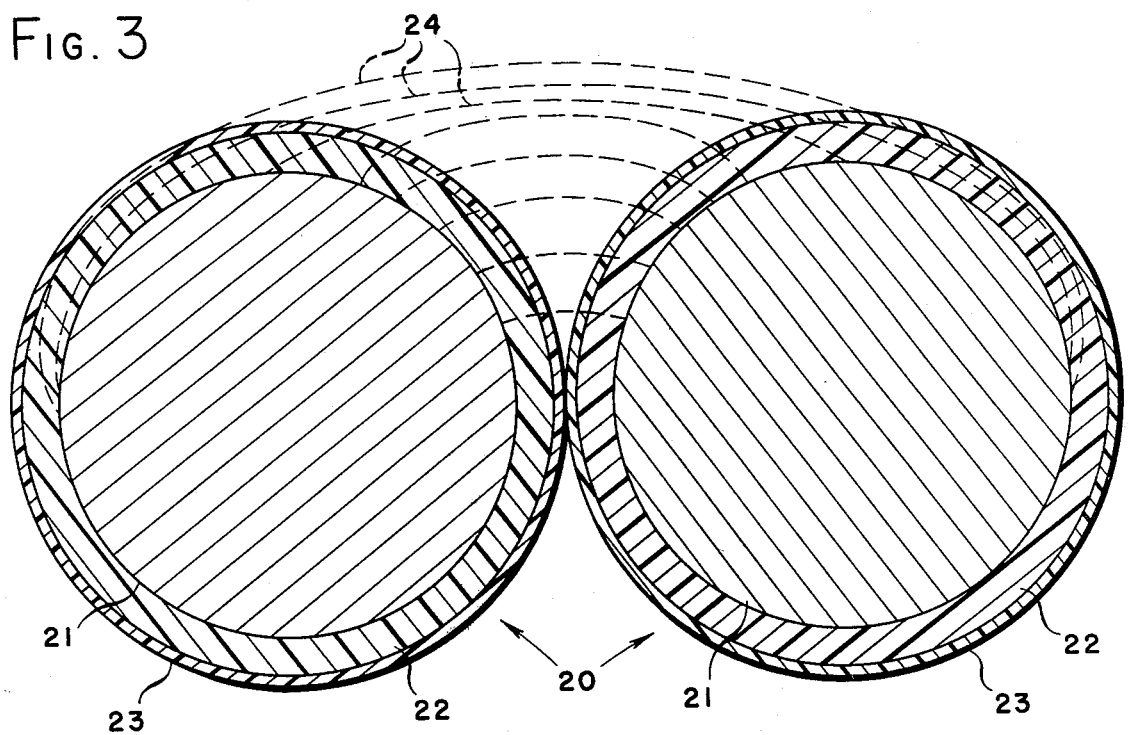
FIG. 3 is an enlarged cross-sectional view of a pair of adjacent probe wires showing the principals of dielectric measurement when the wires are embedded in or mounted on composite materials.

Details of the wires found to be most preferable in the practice of this invention are shown in FIG. 3 comprising a pair of adjacent parallel wires as shown in the FIG. 2 embodiment or twisted wires as discussed below relative to FIGS. 4 and 5. Wires 20 comprise a metallic conductor 21 with a coating 22 consisting of an epoxy enamel or thermosetting polyester coating; such being the typical enamel coated magnet wire as known in the prior art and readily available on the commercial market. The coating 22 of wire 20 may in turn be overcoated by a linear amide-imide coating 23 which is believed to be a nylon substance, and while not critical, outer coating 23 is preferred on those wires used in probe assemblies for carbon and graphite composites to assist in eliminating any penetration of the innercoating 22 by carbon and graphite particles during composite cure which can cause short circuiting. Merely as a typical example, excellent results have been found in the practice of this invention by using a wire 20 having a nominal 0.003" diameter increased to 0.0036" by the addition of insulating coating 22 of thermosetting polyester overcoated with a linear amide-imide coating 23 with such a double coated wire 20 (as readily available on the commercial market) functioning as well in composites without carbon and graphite particles as well as those composites that do contain such carbon and graphite particles.

Numeral 24 identifies the lines depicting the idealized capacitive field between adjacent wires 20 that becomes established upon the supply of alternating current to wires 20.

With these force lines passing through the composite structure surrounding the wires, capacitive changes in the readings reflect changes in the composite dielectric properties caused by water absorption by the composite as well as composite structural degradation resulting from irreversible thermal-shock and fatigue damage. For example, the probe capacitance will increase as water is absorbed by the composite and decrease upon desorbtion of water from the composite, while in the case of composite degradation from fatigue and thermal-shock, the capacitance will increase without decrease of capacitance upon composite cooling since composite degradation resulting from thermal-shock (as well as fatigue) is not reversible to previous levels of dielectric properties.

Figure 4:
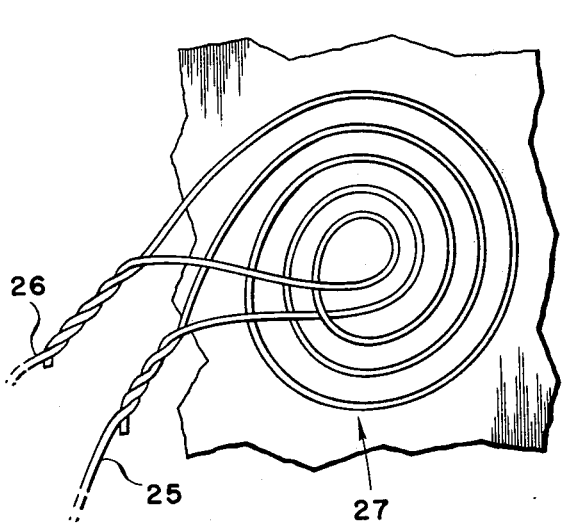
FIGS. 4 and 5 are further embodiments of this invention showing bifilar probe assemblies.
Figure 5:
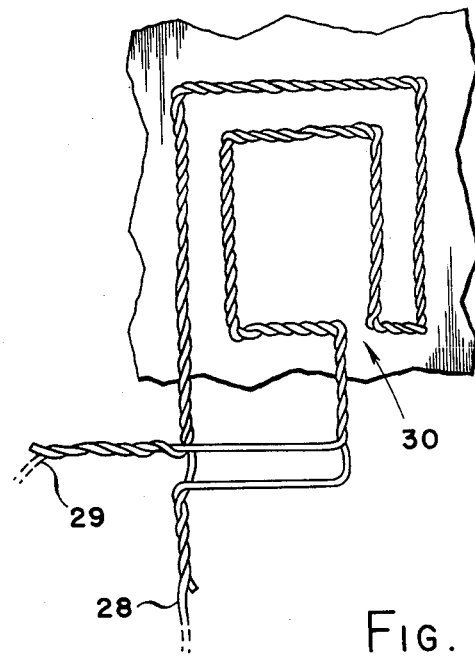

FIGS. 4 and 5 show additional embodiments of this invention wherein the capacitance or dielectric monitoring probe is constructed of a pair of bifilar or twisted wires 25 and 26 formed into a disc coiled shape 27 in FIG. 4 and wires 28 and 29 laid out in a rectangular arrangement 30 as shown in FIG. 5: Both of these probes being laid out in between composite plies during lay-up. Again, by locating the probe configurations of FIGS. 2, 4 and 5 at various interlamellar locations during composite lay-up, an ability to read planar (single layer) conditions is present; and the probes do not impede resin flow or "bleeding" while curing the composite the same as they do not impede moisture into or out of the cured composites. Thusly, this invention provides a most practical and relatively inexpensive arrangement and capability to monitor gradients of moisture content, or, as well as, in addition to, structural degradation of resin matrix composite assemblies after the curing or manufacturing thereof. Also, while not mandatory, the ends of wires 25, 26 in FIG. 4, and wires 28, 29 in FIG. 6 that are not connected to the alternating current source may exit from the composite and be twisted around the wire end that is connected to the alternating current source to give some support thereto toward reducing breakage of thin wires external of the composite through handling and usage. This same approach may further be incorporated with the unconnected wire end of coils 10 in FIG. 1 if desired.

While particular embodiments of the invention have been illustrated and described, it will be obvious to those skilled in the art that various changes and modifications may be made without departure of the invention and it is intended to cover in the appended claims all such modifications and equivalents as fall within the true spirit and scope of this invention.

What is claimed is:

1. A dielectric monitored cured resin matrix composite assembly comprising in combination:
   a multiple-plied, resin matrix composite structure means in a cured state;
   and, a dielectric monitoring means including a first and second capacitive plate means each formed of insulation coated wire having a plate portion and at least one end lead,
   the plate portion of each said wire assembled to the composite structure means whereby at least a portion of the wire insulation throughout the plate portion is in direct physical contact with the composite structure means such that connection of said wire end lead of each of said plate means to an alternating current source produces a measureable electrical capacitance indicative of the existing dielectric value of the composite structure means portion located between said first and second plate means whereby changes in either as well as both moisture content and physical strength level properties of the composite structure means can be determined by changes in the dielectric properties thereof.

2. An assembly as claimed in claim 1 wherein said first and second plate means are assembled to the composite structure means on opposite sides thereof.

3. An assembly as claimed in claim 1 wherein at least one of said first and second plate means is located interlamellarly between two plies of the composite structure means.

4. An assembly as claimed in claim 1 wherein the plate portions of the wires form disc shaped coils.

5. An assembly as claimed in claim 1 wherein the plate portions of the wires form a bifilar disc shaped coil.

6. An assembly as claimed in claim 1 wherein the plate portions of the wires form a twisted bifilar disc shaped coil.

7. An assembly as claimed in claim 1 wherein the plate portions of the wires form a bifilar rectangular layout arrangement.

8. An assembly as claimed in claim 1 wherein the plate portions of the wires form a twisted bifilar rectangular layout arrangement.

9. An assembly as claimed in claim 1 wherein the plate portions of the wires extend longitudinally parallel in side-by-side arrangement.

10. An assembly as claimed in claim 1 wherein the wire insulation comprises a coating from a material group consisting of thermosetting polyester and epoxy enamel.

11. An assembly as claimed in claim 10 wherein the wire insulation includes a linear amide-imide coating over the first coating.

12. A dielectric monitored resin matrix composite assembly comprising in combination:
    a multiple-plied, resin matrix composite means in less than a completely cured state;
    and, a dielectric monitoring means including a first and second capacitive plate means formed of insulation coated wire having a plate portion and at least one end lead,
    the plate portion of each said wire assembled to the composite means whereby at least a portion of the wire insulation throughout the plate portion is in direct physical contact with the composite means such that connection of said wire end lead of each of said plate means to an alternating current source produces a measureable electrical capacitance indicative of the existing dielectric value of the composite means portion located between said first and second plate means whereby changes of the molecular structure by converting from a monomer state to a polymer state in the composite means during cure thereof can be determined by changes in the dielectric properties thereof.

* * * * *